United States Patent [19]

Barber

[11] Patent Number: 4,512,344
[45] Date of Patent: Apr. 23, 1985

[54] ARTHROSCOPIC SURGERY DISSECTING APPARATUS

[76] Inventor: Forest C. Barber, P.O. Box 7744, Fort Worth, Tex. 76111

[21] Appl. No.: 377,403

[22] Filed: May 12, 1982

[51] Int. Cl.³ .............................................. A61B 17/32
[52] U.S. Cl. .................................... 128/305; 128/755
[58] Field of Search ............... 128/305, 276, 213, 303, 128/751, 755

[56] References Cited

U.S. PATENT DOCUMENTS

| | | | |
|---|---|---|---|
| 2,850,007 | 9/1958 | Lingley | 128/305 |
| 3,732,852 | 5/1973 | Banko | 128/305 X |
| 3,882,872 | 5/1975 | Douvas et al. | 128/305 |
| 3,937,222 | 2/1976 | Banko | 128/305 |
| 4,203,444 | 5/1980 | Bonnell | 128/305 X |

*Primary Examiner*—Stephen C. Pellegrino
*Attorney, Agent, or Firm*—Peter J. Murphy

[57] ABSTRACT

An elongated dissecting tool adapted to be driven by a rotary motor is confined within an elongated tool guide which is attached to the rotary motor. A tool is coupled to the motor by means of a suitable chuck; and the tool guide includes bearings for rotationally supporting the elongated dissecting tool. The dissecting tool includes a specially engineered cutting tip at its distal end having at least one longitudinal cutting edge; and this tip is partially enclosed within a shroud formed at the distal end of the guide. The shroud provides an opening for access of the cutting tip to the tissue to be dissected protects adjacent anatomical structures from inadvertent injury, and provides a cutting edge coacting with the cutting edge of the cutting tip for the dissection of soft tissue.

11 Claims, 17 Drawing Figures

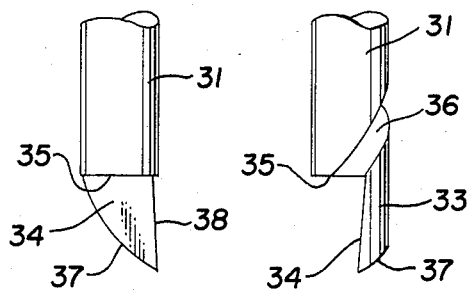
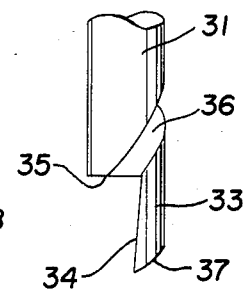
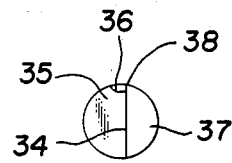
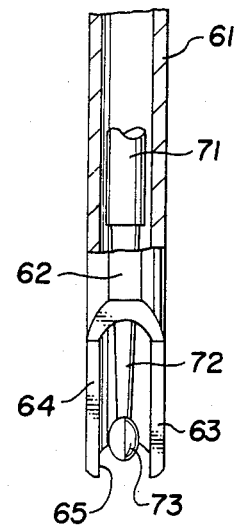
Fig. 10  Fig. 9  Fig. 11  Fig. 16
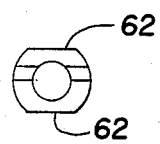
Fig. 13
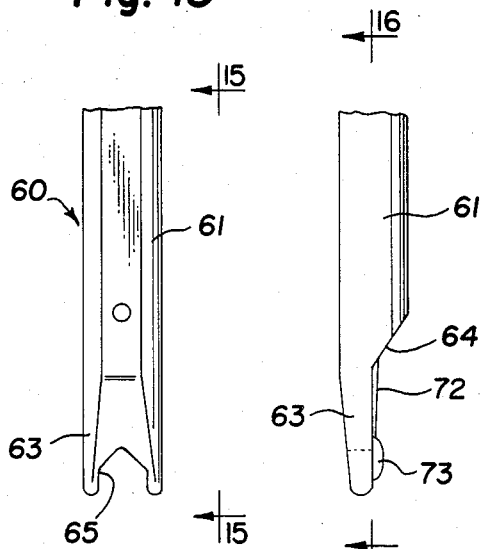
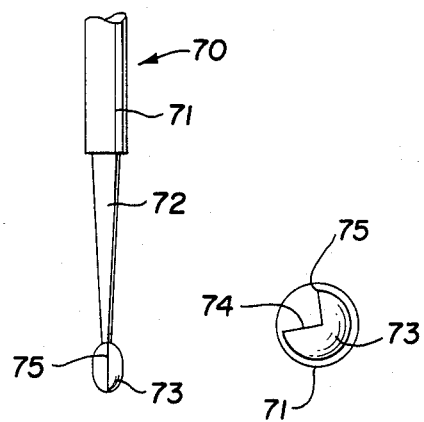
Fig. 12  Fig. 15  Fig. 14  Fig. 17

ARTHROSCOPIC SURGERY DISSECTING APPARATUS

BACKGROUND AND SUMMARY OF THE INVENTION

This invention relates to apparatus for use in the sharp dissection of tissue or bone in arthroscopic surgery and the like; and more particularly to apparatus including a rotary tool adapted to be driven by a rotary motor at speeds sufficient for sharp dissection of anatomical structures.

The invention is concerned particularly with the field of arthroscopic surgery, wherein surgical procedures are performed within the confines of an anatomical joint, for example, without widely opening up or exposing the joint. These procedures are carried out by providing one or several small openings into the anatomical joint, inserting through those openings the probe of an arthroscope which allows the surgeon to visualize the area to be operated, irrigation apparatus to flush out particles of dissected material, and surgical apparatus such as dissecting apparatus.

The arthroscopic dissecting apparatus is used to dissect and cut away soft tissue such as meniscus, synovium and cartilage found within anatomical joints. Since such surgery is frequently performed in a small confined area, the portion of the dissecting apparatus received within the area must be small; and the apparatus must have exactly engineered cutting edges to enable dissection of the desired tissue without injury to adjacent sound anatomical structures.

A principal object of this invention is to provide rotary dissecting apparatus for use in arthroscopic surgery to be driven by a rotary drive motor at elevated rotational speed.

Another object of this invention is to provide such dissecting apparatus having a rotating dissecting tip at its distal end, and having protective means to prevent inadvertent dissection of sound anatomical structures.

A further object of this invention is to provide such apparatus having a rotary dissecting tip adapted to be driven at rotational speeds of 2000 rpm or higher.

Still another object of this invention is to provide such apparatus wherein the dissecting tip is protected by shrouds adapted to guide the tip with respect to the material to be dissected.

These objects are attained in dissecting apparatus which includes broadly a rotatable dissecting tool and a guide for the dissecting tool. The dissecting tool comprises and elongated shank having an axial chuck engageable means at its proximal end and having a dissecting tip at its distal end. The chuck engageable means is adapted to be engaged and rotatably driven by the chuck of a rotary motor. The dissecting tip includes at lease one cutting surface disposed to dissect material with which it is engaged. The guide comprises an elongated hollow shank, enlarged housing means at the proximal end of the shank for attachment to the rotary motor, and protective shroud means formed at the distal end of the shank for partially enclosing the dissecting tip. The shroud means provides an open face for exposing the dissecting tip to the material to be dissected. The guide shank includes bearing means for rotationally supporting the tool shank.

These objects are attained more specifically in such apparatus wherein the guide shank has an axial passage adjacent to its distal end dimensioned slightly larger than the tool shank; and wherein the guide shank is provided with at least one transverse port opening from that passage for the egress of material brought into that passage. The tool shank has an archimedes screw formed adjacent to its distal end for coaction with that guide passage for conveying material to said egress port.

The novel features and the advantages of the invention, as well as additional objects thereof, will be understood more fully from the following description when read in connection with the accompanying drawings.

DRAWINGS

FIG. 9 is an enlarged fragmentary view of the tip end of the tool illustrated in FIG. 6;

FIG. 10 is an enlarged fragmentary view of the tip end of the tool illustrated in FIG. 7;

FIG. 11 is an end view of the tool illustrated in FIGS. 9 and 10;

FIG. 12 is a fragmentary side view of an alternative form of guide according to the invention;

FIG. 13 is an end view of the guide of FIG. 9;

FIG. 14 is a fragmentary side view of an alternative form of dissecting tool according to the invention;

FIG. 15 is a fragmentary side view of the apparatus of FIGS. 11 and 14 as viewed from the plane 15—15 of FIG. 12;

FIG. 16 is a sectional view of the apparatus taken along the line 16—16 of FIG. 15;

FIG. 17 is an end view of the tip of FIG. 14.

DESCRIPTION OF THE PREFERRED EMBODIMENT

In the accompanying drawings there are illustrated two forms of dissecting tools according to the invention, and two forms of dissecting tool guides. The dissecting tools are interchangeable with the guides, and either of the described tools may be used with either of the described guides; however preferred combinations of tools and guides will be described.

FIGS. 1 through 8 illustrate one combination of dissecting tool and tool guide, and also illustrate the manner in which the tool guide is attached to a driving motor.

Figure 1:
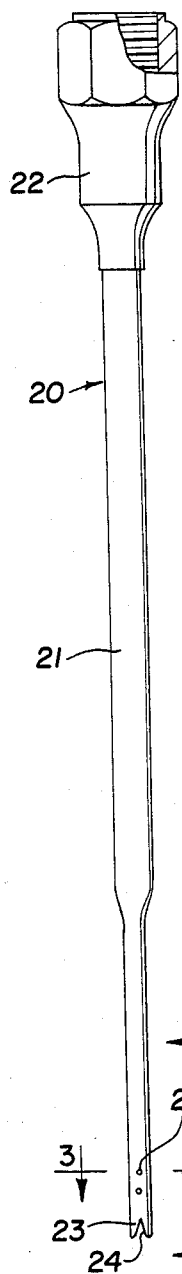
FIG. 1 is a side view of one form of apparatus according to the invention.

FIG. 1 is a side view of a tool guide 20 which consists of an elongated shank 21 having a principal portion of larger cross section, and a tip portion of smaller cross section. An enlarged generally bell-shaped housing 22 is fixed to the proximal end of the shank for attaching the guide to a suitable driving motor. The distal end of the shank 21 is formed to provide a protective shroud 23 for partially enclosing the cutting tip of the dissecting tool as will be described. The housing 22 has an internally threaded axial bore at its proximal end; and the exterior of this housing is hex-shaped to enable application of a servicing wrench.

Figure 2:
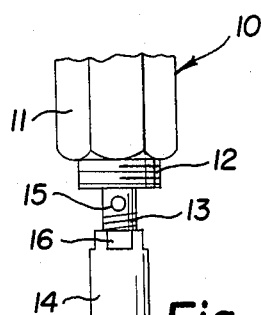
FIG. 2 is a fragmentary side view of a rotary drive motor for the apparatus of FIG. 1.

FIG. 2 is a fragmentary view of a suitable drive motor to which the guide 20 may be attached and for driving the rotating dissecting tool disposed within the guide 20. The motor 10 includes an elongated body 11 having a hex-shaped exterior for application of a suitable manipulating wrench, and having a projecting externally threaded axial boss 12 to be received in the threaded housing 22. The motor drive shaft 13 projects from the boss 12 and is externally threaded to receive a threaded chuck member 14. The motor shaft 13 includes collet fingers (not shown) for enclosing the chuck end of a dissecting tool; and the chuck member 14 includes cam surfaces for compressing the collet fingers against such chuck end. The motor shaft includes a transverse bore 15 and the chuck member includes flats 16 to enable these members to be tightened and loosened relative to each other by suitable tools. For a motor 10 providing right hand rotation of its drive shaft, the boss 12 is preferably provided with left hand threads for coaction with complementary left hand threads of the guide housing 22.

The tip portion of the shank 21 is provided with a V-shaped notch in its distal end face providing a fish-mouth opening 24 for the cutting tip of a dissecting tool. This fish-mouth opening defines opposing extensions of the shank to provide the protective shroud 23; and it will be seen that, in assembled relation with a dissecting tool, the distal end of the dissecting tool is recessed axially relative to the distal end of the shroud 23, to prevent undesired cutting of tissue or bone should the end of the apparatus inadvertently be engaged with anatomical structures within the joint.

Figure 6:
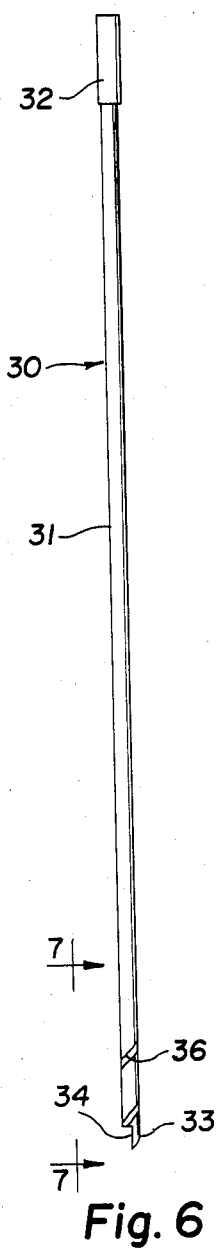
FIG. 6 is a side view of one form of dissecting tool according to the invention.
Figure 4:
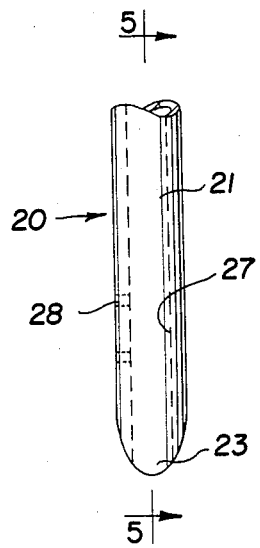
FIG. 4 is a fragmentary side view of the tip end of the apparatus of FIG. 1 as viewed from the plane 4—4 of FIG. 1.
Figure 5:
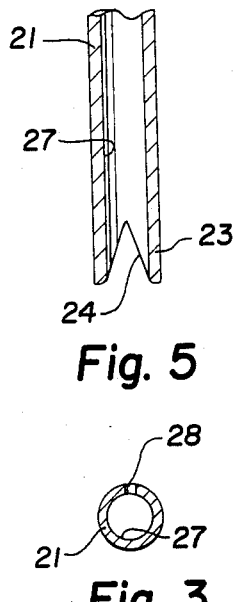
FIG. 5 is a fragmentary sectional view taken along the line 5—5 of FIG. 4.

FIG. 6 is a side view of a dissecting tool 30 which consists of an elongated shank 31, a chuck end 32 at its proximal end dimensioned to be received within the chuck of the driving motor 10, and a cutting tip 33 at the distal end of the shank.

Figure 7:
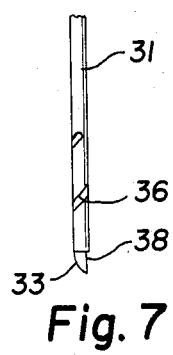
FIG. 7 is a fragmentary side view of the dissecting tip as viewed from the plane 7—7 of FIG. 6.

As best seen in FIGS. 9, 10 and 11, the cutting tip 33 is formed by a tang which projects longitudinally from the distal end of the shank, and may be generally cylindrical in cross section defining a continuation of only one side of the shank. The inner face 34 of the tang forms a juncture with a shoulder 35 formed at the end of the shank. The end face 37 of the tang is beveled arcuately to define a point at its distal end; and a generally longitudinal cutting edge 38 is defined by the juncture of the inner face 34 and the cylindrical outer face of the tang and extends from the distal tip of the tang to the shoulder 35. As best seen in FIGS. 6 and 9, the inner face 34 is provided with a negative rake, relative to a longitudinal plane, extending from the tip end to the shoulder 35; and as seen in FIGS. 7 and 10 the cutting edge 38 is also provided with a negative rake extending from the tip end to the shoulder 35.

Figure 3:
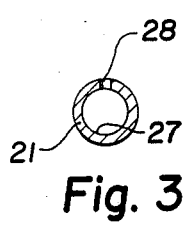
FIG. 3 is a transverse sectional view taken along the line 3—3 of FIG. 1.
Figure 8:
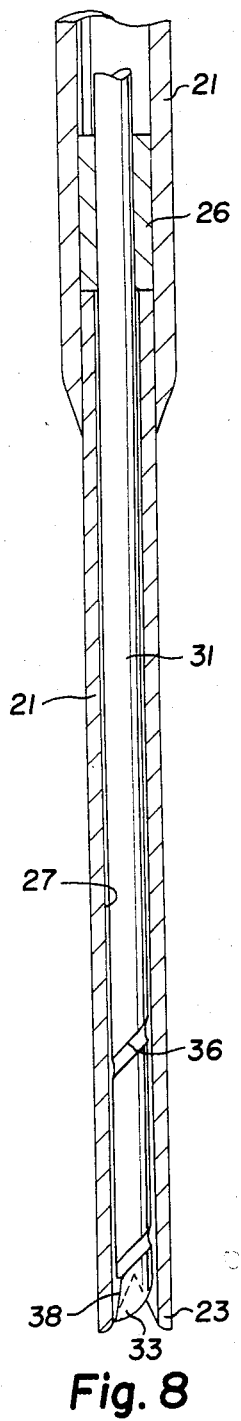
FIG. 8 is a fragmentary longitudinal sectional view of the assembled components shown in FIGS. 1 and 6, including a side view of the dissecting tip of FIG. 6 from the side opposite that shown in FIG. 7.

The tool shank 31 is provided with a spiral groove 36, beginning at the cutting tip 33, which spiral groove defines an archimedes screw for coaction with the guide 20 as will be described. As seen in FIGS. 6, 8, 9 and 11, this groove 36 begins at the juncture of the shoulder 35 and the cutting edge 38, for a purpose to be described subsequently. FIG. 8 is a fragmentary longitudinal sectional view of the assembly of the guide 20 and dissecting tool 30. The larger portion of the guide shank 21 includes at least one bearing 26 for rotationally supporting the shank of the tool. It will be seen that the tip portion of the shank 21 includes a longitudinal passage 27 which is slightly larger in diameter than the diameter of the shank 31 of the cutting tool, thereby providing a clearance between the shanks of the assembled guide and tool. Referring particularly to FIGS. 1 and 3, it will be seen that the tip end of the shank 21 is provided with two transverse ports 28 communicating the passage 27 with the exterior of the shank tip.

The fish-mouth opening of this guide 20 enables the apparatus to be guided in a manner that a thin line of tissue may be received within the opening and dissected by the dissecting tool 30. With clockwise rotation of the tool 30 relative to the guide 20, it will be seen that the tip end of the tang cutting edge 38 will first engage the tissue and start microscopic cutting of the tissue. The negative rakes of both the cutting edge 38 and the tang inner face 34 will cause the tissue to be drawn longitudinally inward from the tip end of the tool to be dissected by the entire length of the cutting edge 38. It will also be seen that the tool cutting edge 38 coacts with the V-notches of the fish mouth opening to provide a shearing action for the cutting away of tissue received within the notch. It will be seen, then, that the cut away tissue particles are drawn toward the distal end of the spiral groove 36, and that the screw action of the archimedes screw 36 will convey this material, including fluids and solid particles, to the ports 28 from which that material may egress from the apparatus.

FIGS. 12 through 17 illustrate a different combination of guide 60 and dissecting tool 70 according to the invention. The guide 60 is identical to the previously described guide 20 except for the configuration of the tip end of the guide shank 61 and the shroud 63. The tip portion of the shank is generally cylindrical, but is provided with opposed flats 62 to provide a generally oval cross section as seen in FIG. 13. To provide an opening for exposure of the cutting tip of the dissecting tool, a portion of the distal end of the shank 61 is removed along one side of an axial plane, so that a generally arcuate hood is provided by the remaining portion which projects from the distal end to define the shroud 63; and the removed or notched portion 64 defines the opening for exposing the cutting tip. This distal end of the shroud 63 is provided with an end opening V-notch 65 which functions in a manner similar to the fish-mouth notch 24 of the guide 20 to guide the apparatus in the dissecting of a thin line of tissue.

FIG. 14 is a fragmentary side view of the distal end portion of a dissecting tool 70 which consists of an elongated shank including a reduced diameter tip portion 71, a still further reduced diameter neck 72 at the distal end of the shank, and an enlarged cutting head 73 at the distal end of the neck 72 which head is generally ovoid in shape. The head 73 is provided with a generally longitudinal flute 74 which defines, with the exterior surface of the head 73, a specifically engineered cutting edge 75. It will be seen in FIGS. 15 and 16 that, in assembled relation, the distal end of the shroud 63 projects beyond the distal end of the cutting tip 73 to provide for maximum protection of sound tissues by the shroud 63.

The dissecting tool 70 may be used for less aggressive dissecting than that of the dissecting tool 30.

What has been described is a unique apparatus for performing a variety of surgical procedures in arthroscopic surgery.

While preferred embodiments of the invention have been illustrated and described, it will be understood by those skilled in the art that changes and modifications may be resorted to without departing from the spirit and scope of the invention.

What is claimed is:

1. Arthroscopic sharp dissecting apparatus comprising
    a rotatable dissecting tool comprising an elongated shank having an axial chuck engageable means at its proximal end and having a dissecting tip at its distal end; said chuck engageable means adapted to be engaged and rotatably driven by the chuck of a rotary motor; said dissecting tip including at least one cutting edge disposed to dissect material with which it is engaged;
    a guide for said dissecting tool comprising an elongated hollow shank, means at the proximal end of said shank for attachment to said rotary motor, and protective shroud means formed at the distal end of said shank for partially enclosing said dissecting tip; said guide shank having a generally V-shaped notch formed at its distal end, opening longitudinally to said distal end at one side wall thereof, for exposing said dissecting tip to the material to be dissected;
    said shank including means for rotationally supporting said tool shank.

2. Arthroscopic sharp dissecting apparatus comprising
    a rotatable dissecting tool comprising an elongated shank having an axial chuck engageable means at its proximal end and having a dissecting tip at its distal end; said chuck engageable means adapted to be engaged and rotatably driven by the chuck of a rotary motor; said dissecting tip including at least one cutting edge disposed to dissect material with which it is engaged;
    a guide for said dissecting tool comprising an elongated hollow shank, means at the proximal end of said shank for attachment to said rotary motor, and protective shroud means formed at the distal end of said shank for partially enclosing said dissecting tip; said guide shank having a notch formed at its distal end, at one side wall thereof, for exposing said dissecting tip to the material to be dissected;
    said shank including means for rotationally supporting said tool shank;
    said guide shank having an axial passage adjacent to its distal end; and said guide shank being provided with at least one transverse port, opening from said passage for egress of material drawn into said passage;
    said tool shank having a special groove formed adjacent to its distal end for conveying material to said egress port.

3. Apparatus as set forth in claim 1
    said guide shank having opposed notches formed in its distal end defining a fish mouth opening for exposing the dissecting tip of said tool.

4. Arthroscopic sharp dissecting apparatus comprising
    a rotatable dissecting tool comprising an elongated shank having an axial chuck engageable means at its proximal end and having a dissecting tip at its distal end; said chuck engageable means adapted to be engaged and rotatably driven by the chuck of a rotary motor; said dissecting tip including at least one cutting edge disposed to dissect material with which it is engaged;
    a guide for said dissecting tool comprising an elongated hollow shank, means at the proximal end of said shank for attachment to said rotary motor, and protective shroud means formed at the distal end of said shank for partially enclosing said dissecting tip; said guide shank having a notch formed at its distal end, at one side wall thereof, for exposing said dissecting tip to the material to be dissected;
    said shank including means for rotationally supporting said tool shank;
    said tool having a tang extending longitudinally from the distal end of its shank, defining said dissecting tip; said tang having a generally longitudinal cutting edge for engaging the material to be dissected.

5. Apparatus as set forth in claim 1
    said tool having a reduced diameter axial neck at the distal end of said shank, and an enlarged generally ovoid head at the distal end of said neck, said neck and head defining said dissecting tip; and said head having at least one generally longitudinal flute defining a cutting edge.

6. Arthroscopic sharp dissecting apparatus comprising
    a rotatable dissecting tool comprising an elongated shank having an axial chuck engageable means at its proximal end and having a dissecting tip at its distal end; said chuck engageable means adapted to be engaged and rotatably driven by the chuck of a rotary motor; said dissecting tip including at least one cutting edge disposed to dissect material with which it is engaged;
    a guide for said dissecting tool comprising an elongated hollow shank, means at the proximal end of said shank for attachment to said rotary motor, and protective shroud means formed at the distal end of said shank for partially enclosing said dissecting tip; said guide shank having a notch formed at its distal end, at one side wall thereof, for exposing said dissecting tip to the material to be dissected;
    said shank including means for rotationally supporting said tool shank;
    said notch defining a cutting edge coacting with said cutting edge of said dissecting tip to dissect tissue entering said notch.

7. Apparatus as set forth in claim 4
    said tool shank having a cylindrical surface; and said tang cutting edge being formed at said cylindrical surface.

8. Apparatus as set forth in claim 7
    said tool shank having an inner, generally planar face oriented with a negative rake relative to a longitudinal plane.

9. Apparatus as set forth in claim 7
    said tool cutting edge having a negative rake.

10. Apparatus as set forth in claim 7
    said tool shank having a spiral groove formed adjacent to its distal end; the distal end of said groove being disposed adjacent to said tang cutting edge at the base of said tang; and said guide shank having at least one transverse port spaced axially from its distal end, for coaction with said spiral groove of said tool to discharge material carried within said spiral groove.

11. Apparatus as set forth in claim 4 said guide shank having at least one tang extending longitudinally from its distal end, defining said shroud means for enclosing partially said dissecting tip; said tang defining a cutting edge coacting with said cutting edge of said dissecting tip to produce a shearing action.

* * * * *